(12) United States Patent  
Ng et al.

(10) Patent No.: US 10,036,703 B1  
(45) Date of Patent: Jul. 31, 2018

(54) PORTABLE LASER BIOSENSOR

(71) Applicant: The United States of America as represented by the Secretary of the Navy, Washington, DC (US)

(72) Inventors: Kin Chiu Ng, Fresno, CA (US); Subrata Sanyal, Eastvale, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/712,120

(22) Filed: Sep. 21, 2017

Related U.S. Application Data

(60) Provisional application No. 62/451,216, filed on Jan. 27, 2017.

(51) Int. Cl.
| | |
|---|---|
| *G01N 21/00* | (2006.01) |
| *G01N 21/64* | (2006.01) |
| *G01N 21/31* | (2006.01) |
| *G01N 30/00* | (2006.01) |
| *G01N 21/65* | (2006.01) |

(52) U.S. Cl.
CPC ..... *G01N 21/6402* (2013.01); *G01N 21/3103* (2013.01); *G01N 21/65* (2013.01); *G01N 2030/0095* (2013.01)

(58) Field of Classification Search
CPC ...... G01J 3/02; G01J 3/00; G01J 3/44; G01N 21/65; G01N 21/64; G01N 21/645; G01N 2021/64; G01N 21/31
See application file for complete search history.

(56) References Cited

U.S. PATENT DOCUMENTS

| | | | |
|---|---|---|---|
| 6,091,502 A | * | 7/2000 | Weigl ............... G01N 27/44721 356/416 |
| 6,255,118 B1 | | 7/2001 | Alfano et al. |
| 7,236,243 B2 | | 6/2007 | Beecroft et al. |
| 7,286,222 B2 | | 10/2007 | Gardner, Jr. |
| 7,636,154 B1 | | 12/2009 | LaValley et al. |
| 7,851,251 B2 | | 12/2010 | Tseng et al. |
| 8,502,168 B1 | | 8/2013 | Poteet et al. |
| 8,548,174 B2 | | 10/2013 | Dufresne et al. |
| 8,729,502 B1 | | 5/2014 | Klotzkin |
| 8,849,380 B2 | | 9/2014 | Patwardhan |
| 9,255,900 B2 | | 2/2016 | Fishbine et al. |
| 2016/0084707 A1 | | 3/2016 | Scott et al. |

FOREIGN PATENT DOCUMENTS

WO   WO 2015/061793   4/2015

OTHER PUBLICATIONS

Hossain et al., "Combined 'dual' Absorption and Fluorescence Smartphone Spectrometers", Optics Letters, vol. 40, No. 8, Apr. 15, 2015, retrieved on Jun. 24, 2016 from http://www.osapublishing.org/ol/abstract.cfm?uri=40-8-1737.pdf.

(Continued)

*Primary Examiner* — Abdullahi Nur  
(74) *Attorney, Agent, or Firm* — Christopher A. Monsey

(57) ABSTRACT

A hand-held laser based biosensor including modular components, combining absorption spectrophotometry and molecular fluorescence spectrophotometry, and including a sample cell module having an improved absorption path length.

46 Claims, 8 Drawing Sheets

(56) References Cited

OTHER PUBLICATIONS

Baird et al., "Compact, Self-Contained Optical Spectrometer", Applied Spectroscopy, vol. 49, No. 11, 1995, pp. 1699-1704, retrieved on Jun. 24, 2016 from http://www.osapublishing.org/as/abstract.cfm?uri=as-49-11-1699.pdf.

Ocean Optics, "Maya2000Pro Data Sheet for Versions 3.00.1 and Above", retrieved on Jun. 23, 2016 from http://oceanoptics.com/wp-content/uploads/OEM-Data-Sheet-Maya2009Prov3.pdf.

Horiba Scientific, "Fluorolog-3, How to build a Spectrofluorometer", retrieved on Jun. 24, 2016 from http://horiba.com/fileadmin/uploads/Scientific/Documents/Fluorescence/flogcat.pdf.

Soper et al., "Molecular Fluorescence, Phosphorescence, and Chemiluminescence Spectrometry", Analytical Chemistry, vol. 66, No. 12, Jun. 15, 1994, retrieved on Jun. 23, 2016 from http://pubs.acs.org/dei/abs/10.1021/ac00084a016?journalCode+ancham&.pdf.

Strianese et al., "Absorption into Fluorescence. A method to sense biologically relevant gas molecules", Nanoscale, 2011, 3, 298-302, retrieved on Jun. 23, 2016 from http://www.ncbi.nlm.nih.gov/pubmed/21060958.pdf.

Clark et al., "Biological Detection System Technologies—Technology and Industrial Base Study", Feb. 2001, retrieved on Jun. 23, 2016 from http://www.acq.osd.mil/mibp/natibo/docs/BioDetectReport-2.pdf.

Thrush et al., "Integrated bi-fluorescence sensor", Journal of Chromatography 1013 (2003) 103-110, retrieved on Jun. 23, 2016 from http://www.breault.com/sites/default/files/knowledge_base/wp_els_001_integrated_bio-fluorescence.pdf.

So et al., "Fluorescence Spectrophotometry", Encyclopedia of Life Sciences, 2002, retrieved on Jun. 23, 2016 from http://web.mit.edu/solab/Documents/Assets/So-Fluorescence%20pectrophotometry.pdf.

Cetin et al., "Handheld high-throughput plasmonic biosensor using computational on-chip imaging", Light: Science & Applications, 2014, retrieved on Jun. 23, 2016 from http://www.nature.com/lsa/journal/v3/nl/pdf/lsa20143a.pdf.

\* cited by examiner

US 10,036,703 B1

PORTABLE LASER BIOSENSOR

CROSS-REFERENCE TO RELATED APPLICATION

The present application claims priority to U.S. Provisional Patent Application Ser. No. 62/451,216, filed Jan. 27, 2017, the disclosure of which is expressly incorporated herein by reference.

STATEMENT REGARDING FEDERALLY SPONSORED RESEARCH OR DEVELOPMENT

The invention described herein includes contributions by one or more employees of the Department of the Navy made in performance of official duties and may be manufactured, used, and licensed by or for the United States Government without payment of any royalties thereon. This invention (Navy Case 200,408) is assigned to the United States Government and is available for licensing for commercial purposes. Licensing and technical inquiries may be directed to the Technology Transfer Office, Naval Surface Warfare Center Corona Division, email: CRNA_CTO@navy.mil.

BACKGROUND AND SUMMARY OF THE DISCLOSURE

The present disclosure relates generally to methods and apparatuses for detecting and identifying substances within a sample fluid. More particularly, the present invention relates to a portable, illustratively pocket wearable, laser based biosensor including modular components, and combining molecular absorption spectrophotometry and molecular fluorescence spectrophotometry.

Molecular absorption spectrophotometry (MAS) and molecular fluorescence spectrophotometry (MFS) are well established analytical techniques. More particularly, a variety of dedicated molecular absorption spectrophotometers and dedicated molecular fluorescence spectrophotometers are available from a variety of chemical instrument manufacturers. Some of these devices are portable. While simultaneous operation of MAS and MFS has been performed in research laboratories for solving specialized, fundamental problems; there are no known portable combination absorption-fluorescence spectrophotometers available in the market for the field testing of substances within a fluid sample.

There remains a need for the efficient field testing of substances within a fluid sample, combining both molecular absorption spectrophotometry (MAS) and molecular fluorescence spectrophotometry (MFS), in a single spectrophotometer, for performing both absorption and fluorescence measurements and providing rapid results to the user.

The present invention relates to a hand-held laser based biosensor that illustratively is portable (e.g., pocket wearable by a user), is modular (e.g., interchangeable modules), has improved selectivity (e.g., combined molecular absorption spectrophotometry and molecular fluorescence spectrophotometry), and has improved sensitivity (e.g., long absorption path length and long emission (fluorescence) region). Such a biosensor may find use in a variety of applications including, for example, in the military, food and drug industries, and with first responders (e.g., police and firefighters).

According to an illustrative embodiment of the present disclosure, a hand-held biosensor includes a radiation emitting module including light emitting module housing, and a light source received within the radiation emitting module housing and configured to generate excitation energy, illustratively a laser beam. The hand-held biosensor further includes a sample cell module including a sample cell module housing defining a chamber configured to receive a solution, a sample inlet in fluid communication with the chamber, and a waste outlet in fluid communication with the chamber. A first releasable coupling is positioned between the radiation emitting module and the sample cell module. An absorption detector is configured to detect emission intensity produced by the electromagnetic radiation passing through the solution in the sample cell chamber and produce absorption spectral data in response thereto, and produce absorption spectral data in response thereto, the absorption detector including an absorption detector spectral filter. A fluorescence detector is configured to detect molecular emissions produced by the laser excited molecules as the laser beam passes through the solution in the sample cell chamber and produces fluorescence spectral data in response thereto, the fluorescence detector including a fluorescence detector spectral filter. A processor is in electrical communication with the absorption detector and the fluorescence detector, the processor being configured to receive the absorption spectral data from the absorption detector and the fluorescence spectral data from the fluorescence detector. A display module is in electrical communication with the processor, the display module including a display module housing, an absorption display supported by the display module housing and configured to provide an indication of the absorption spectral data from the absorption detector, and a fluorescence display supported by the display module housing and configured to provide an indication of a fluorescence spectral data from the fluorescence detector. A power source is in communication with the processor. A second releasable coupling is positioned between the display module and the sample cell module.

According to another illustrative embodiment of the present disclosure, a hand-held biosensor includes an outer casing extending between a proximal end and a distal end, and a radiation emitting module supported proximate the proximal end of the outer casing. A display module is supported proximate the distal end of the outer casing, and the sample cell module is supported intermediate the radiation emitting module and the display module. The sample cell module includes a sample cell module housing defining a chamber and including a light entry port, a light exit port axially spaced by the chamber from the light entry port, a longitudinal axis defined by the light entry port and the light exit port, and a reflective surface configured to reflect light from the radiation emitting module transverse to the longitudinal axis. The hand-held biosensor further includes an absorption detector, a fluorescence detector, and a processor in electrical communication with the absorption detector and the fluorescence detector, the processor being configured to receive absorption spectral data from the absorption detector and fluorescence spectral data from the fluorescence detector. The sample cell module includes an axial length between the light entry port and the light exit port, the axial length being at least about 5 centimeters.

According to another illustrative embodiment of the present disclosure, a method of constructing a hand-held biosensor includes the steps of providing a sample cell module including a sample cell module housing having a side wall defining a chamber and extending longitudinally between a proximal end and a distal end, a sample inlet in communication with the chamber, and a waste outlet in communication with the chamber. The method further includes the steps of providing a solution within the chamber of the sample cell module, providing a radiation emitting module including a radiation emitting module housing extending longitudinally between the proximal end and the distal end, a light source received within the radiation emitting module housing and configured to generate an excitation laser beam, and releasably coupling the distal end of the radiation emitting module housing to the proximal end of the sample cell module housing. The method further includes the steps of providing an absorption detector at the distal end of the sample cell, the absorption detector configured to detect the intensity of the laser beam (energy) passing through the solution in the sample cell chamber, the absorption detector including an absorption detector spectral filter, and providing a fluorescence detector configured to detect emissions produced by laser excited molecules as the laser beam passes through the solution of the sample cell chamber, the fluorescence detector including a fluorescence detector spectral filter. The method also includes the steps of providing a processor in electrical communication with the absorption detector and the fluorescence detector, the processor configured to receive absorption spectral data from the absorption detector and fluorescence spectral data from the fluorescence detector. The method further includes the steps of providing a display module in electrical communication with the processor, the display module including the display module housing extending between a proximal end and a distal end, an absorption display supported by a display module housing and configured to provide an indication of the absorption spectral data, and a fluorescence display supported by the display module housing and configured to provide an indication of the fluorescence spectral data. The method further includes the steps of releasably coupling the distal end of the sample cell module housing to the proximal end of the display module housing, and providing a power source in electrical communication with the processor.

According to further illustrative embodiment of the present disclosure, a method of detecting a substance within a fluid sample using a hand-held biosensor includes the steps of providing a sample cell module including a sample cell module housing having a side wall defining a chamber and extending along a longitudinal axis between a proximal end and a distal end, a sample inlet in fluid communication with the chamber, and a waste outlet in fluid communication with the chamber, and fluidly coupling a waste collection vial to the waste outlet. The method further includes the steps of injecting a sample solution through the sample inlet into the chamber of the sample cell module, and generating an electromagnetic radiation with a laser light source. The method also includes the steps of directing the electromagnetic radiation through the sample solution in the chamber of the sample cell, absorbing the electromagnetic radiation by the sample solution, sensing the intensity of the electromagnetic radiation absorbed by the sample solution by an absorption detector, and generating an absorption signal of interest from the absorption detector. The method further includes the steps of producing fluorescence emissions from the sample solution, sensing the fluorescence emissions by a fluorescence detector, and generating a fluorescence signal of interest from the fluorescence detector. The method also includes steps of displaying an indication of the absorption signal of the absorption display, and displaying an indication of the fluorescence signal on the fluorescence display.

Additional features and advantages of the present invention will become apparent to those skilled in the art upon consideration of the following detailed description of the illustrative embodiments exemplifying the best modes of carrying out the invention as presently perceived.

BRIEF DESCRIPTION OF THE DRAWINGS

A detailed description of the drawings particularly refers to the accompanying figures, in which.

DETAILED DESCRIPTION OF THE DRAWINGS

Various embodiments of the invention described herein are not intended to be exhaustive or to limit the invention to precise forms disclosed. Rather, the embodiments selected for description have been chosen to enable one skilled in the art to practice the invention.

Figure 1:
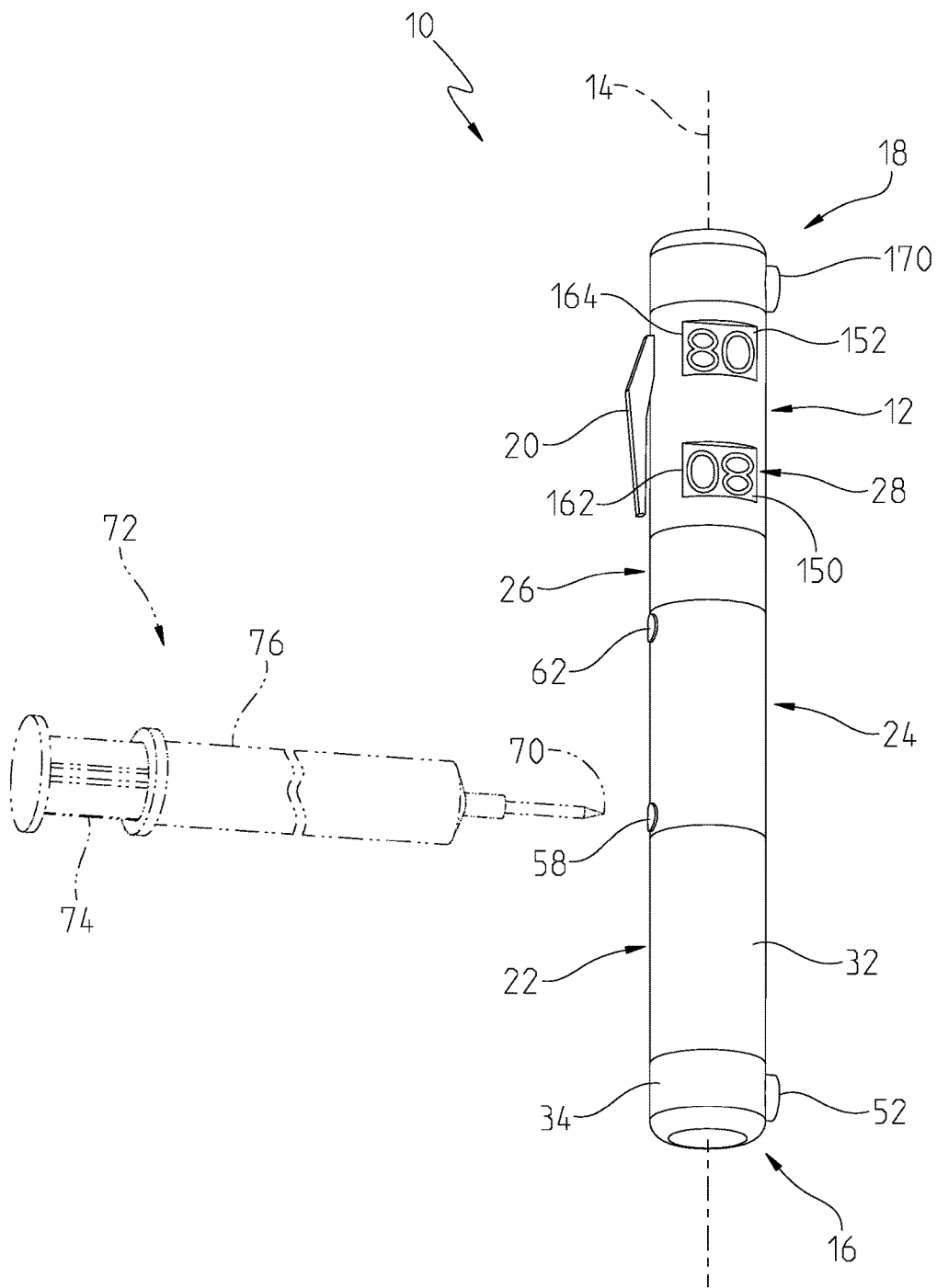
FIG. 1 is a perspective view of an illustrative portable, illustratively pocket wearable, biosensor of the present disclosure.
Figure 2:
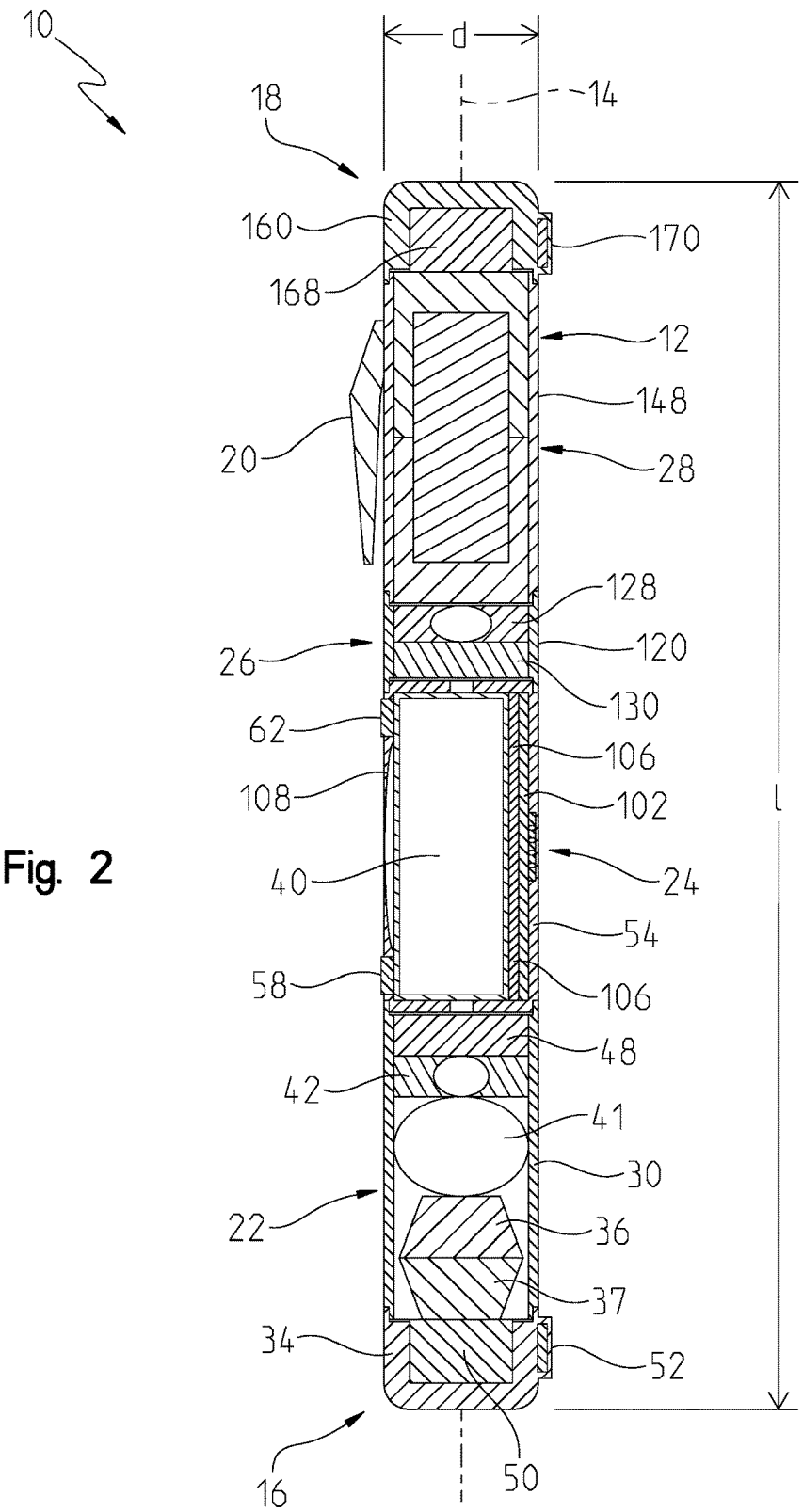
FIG. 2 is a longitudinal cross-sectional view of the biosensor of FIG. 1.

Referring initially to FIGS. 1-4, an illustrative hand-held biosensor 10 is shown for use in detecting substances (e.g., biological molecules, often referred to as biomolecules or bio-agents) within a sample fluid (e.g., gas or liquid). Illustratively, the biosensor 10 includes an outer casing 12 extending along a longitudinal axis 14 between a proximal (or lower) end 16 and a distal (or upper) end 18. The biosensor 10 is configured to have an ergonomic size, shape and weight, thereby facilitating operation by a user. With reference to FIG. 2, the outer casing 12 is configured to have dimensions substantially like that of a conventional laser pointer and, as such, is small enough to be used or operated while being held in the hand or hands of a user, and may be stored within a conventional pocket of the user. More particularly, the outer casing 12 is illustratively cylindrical and has an axial length (l) of less than about 20 centimeters (7.87 inches) and an outer diameter (d) of less than about 4 centimeters (1.57 inches). In a further illustrative embodiment, the outer casing 12 has an axial length (l) of less than about 16 centimeters (6.30 inches) and an outer diameter (d) of less than about 3 centimeters (1.18 inches). In one illustrative embodiment, the outer casing 12 has an axial length (l) of approximately 14.2 centimeters (5.6 inches), and an outer diameter (d) of approximately 2 centimeters (0.79 inches). A representative weight of the hand-held biosensor 10 is approximately 4 ounces. An external clip 20 is illustratively coupled proximate the distal end 18 of the outer casing 12 for coupling to clothing of a user, for example to a shirt pocket (not shown).

The biosensor 10 illustratively includes a plurality of releasably coupled component sections or modules, including a radiation emitting module 22, a sample cell module 24, an absorption detector module 26, and a display module 28, all aligned along the longitudinal axis 14. Illustratively, the radiation emitting module 22 is positioned adjacent the proximal end 16 of the biosensor 10, and the display module 28 is positioned adjacent the distal end 18 of the biosensor 10.

Figure 3:
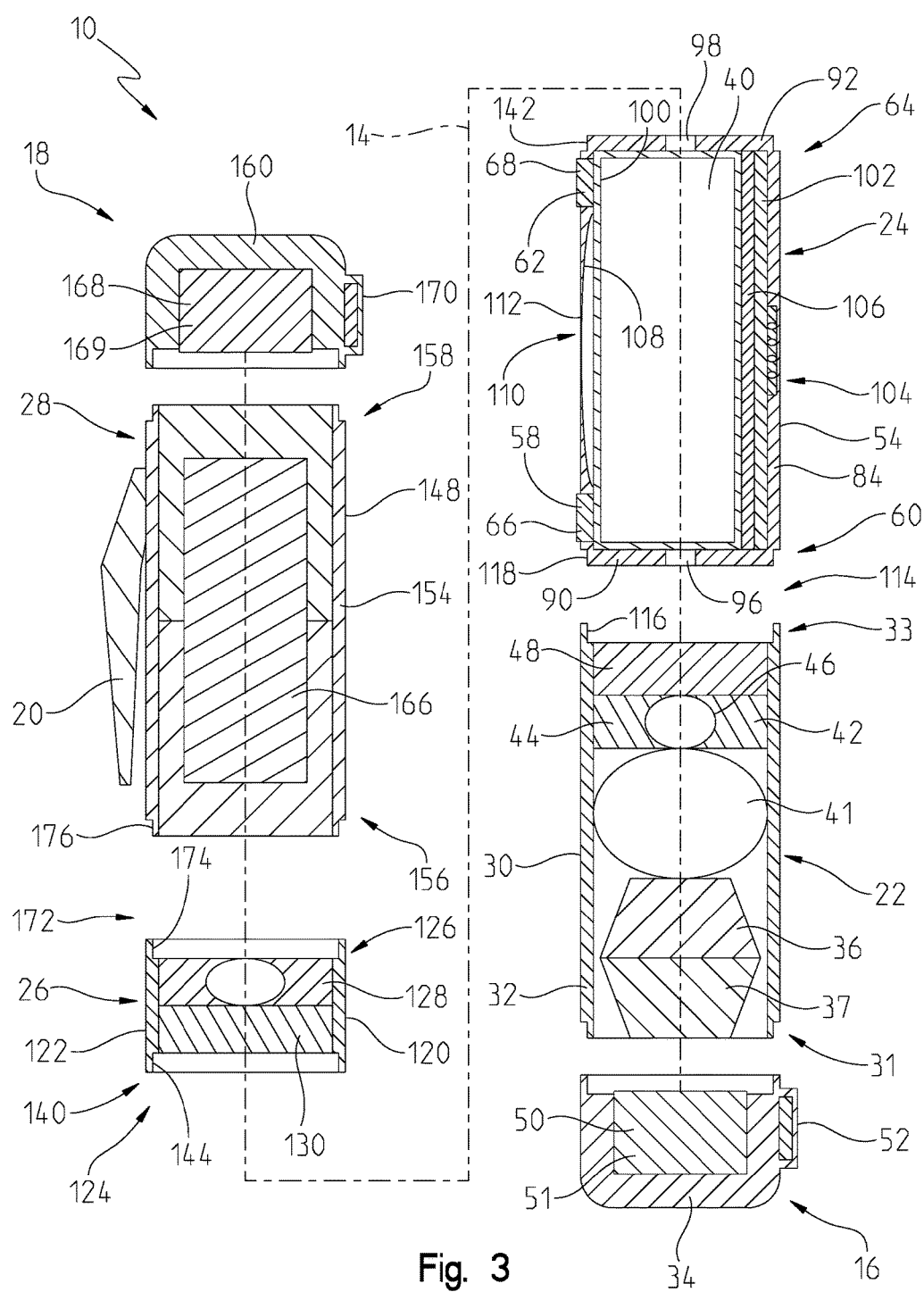
FIG. 3 is an exploded longitudinal cross-sectional view of the biosensor of FIG. 2.
Figure 4:
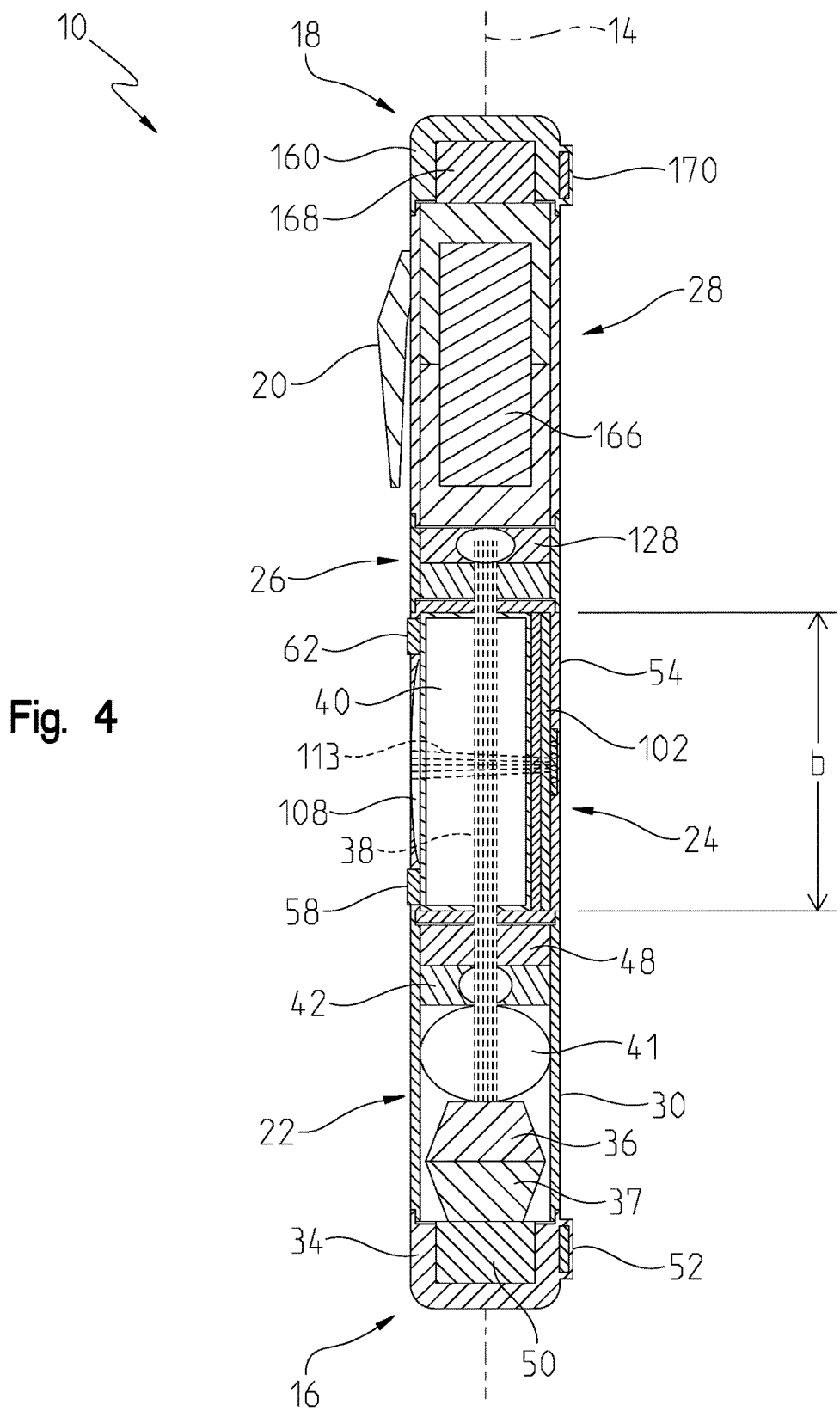
FIG. 4 is a cross-sectional view similar to FIG. 2, showing the light source emitting an excitation energy, illustratively a laser beam passing through a sample chamber to an absorption detector and a reflective surface reflecting fluorescence to a fluorescence detector.
Figure 5:
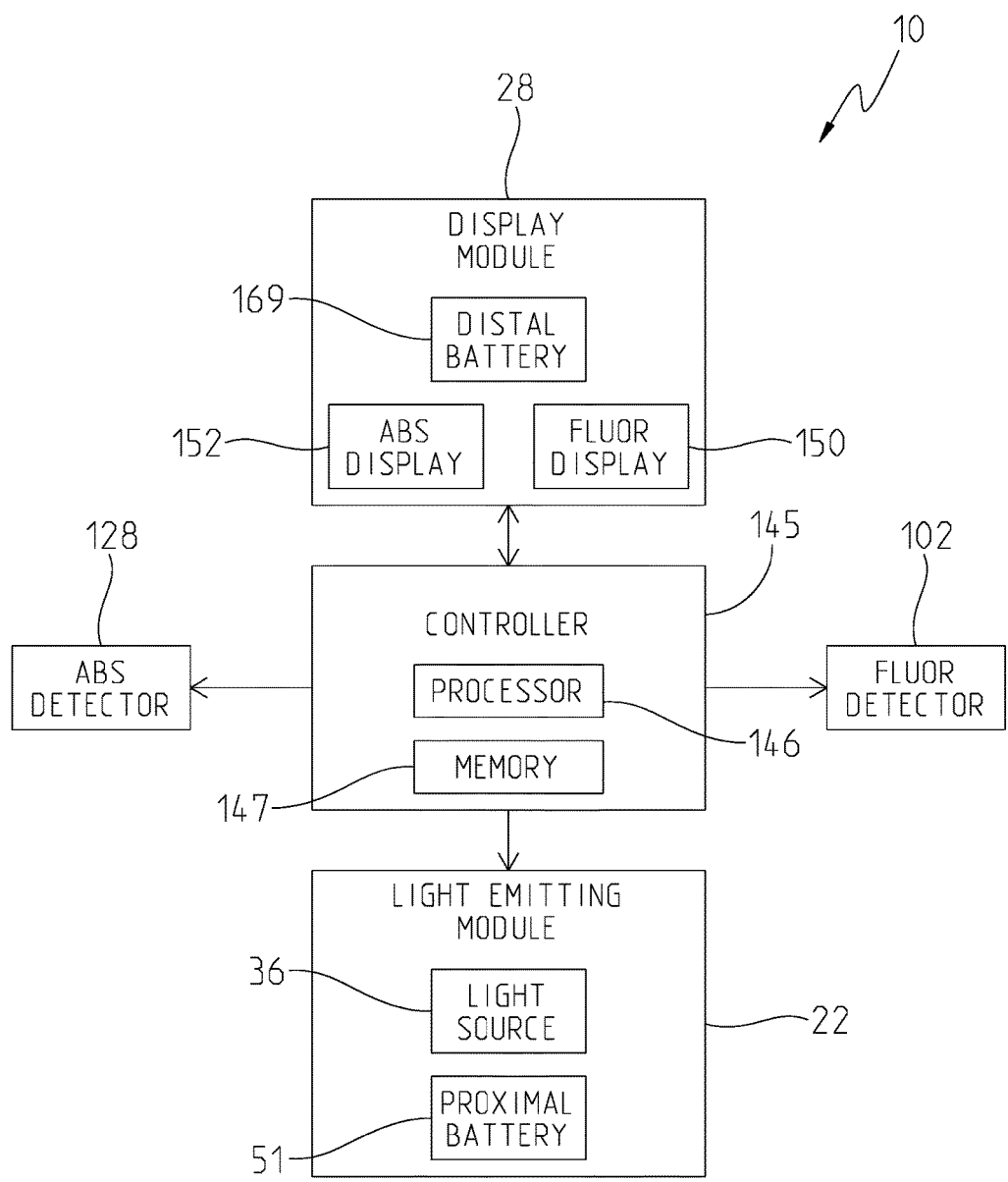
FIG. 5 is a block diagram illustrating interaction between various components of the biosensor of FIG. 1.

With reference to FIGS. 3 and 4, the radiation emitting module 22 illustratively includes a radiation emitting module housing 30 having a cylindrical side wall 32 extending between a proximal end 31 and a distal end 33. An end cap 34 is illustratively threadably coupled to the proximal end 31 of the side wall 32. Both the side wall 32 and the end cap 34 are illustratively formed of a durable, light weight material, such as anodized aluminum or thermoplastic.

The radiation emitting module 22 is configured to emit electromagnetic radiation (e.g., laser light) toward the sample cell module 24. Illustratively, a radiation source, such as a laser diode 36 and a laser diode driver 37 are positioned within the radiation emitting module housing 30 and is configured to emit electromagnetic radiation. More particularly, the laser diode 36 is configured to emit an ultraviolet radiation laser beam 38 in an axial direction (i.e., along the longitudinal axis 14 as shown in FIG. 4) toward a sample cell chamber 40 defined by the sample cell module 24. As further detailed herein, in an illustrative universal embodiment of biosensor 10, the wavelength of the laser beam 38 emitted by the laser diode 36 is illustratively between 260 nm and 290 nm, and more particularly about 275 nm, for native absorption and native fluorescence. In an illustrative selective embodiment of biosensor 10, the wavelength of the laser beam 38 emitted by the laser diode 36 will be centered approximately at the excitation wavelength for absorption and fluorescence of the labeled biomolecule. The laser diode 36 is illustratively soldered to the laser diode driver 37. Illustratively, a suitable laser diode driver 37 is the CW Laser Diode Driver LSC-025 (0.82 inches×0.29 inches× 0.20 inches), available from Laser Components USA, Inc. of Bedford, N.H.

A lens 41 is illustratively positioned proximate to, and distal of, the laser diode 36. More particularly, the lens 41 is positioned between the laser diode 36 and the sample cell chamber 40. The illustrative laser diode driver 37 is operably coupled to and positioned proximal of the laser diode 36. The lens 41 may be of conventional design (e.g., formed of a quartz material) and is used for collimating the laser beam 38 to within a desired diameter, illustratively less than about 3 millimeters.

A spatial filter 42 is illustratively positioned distal of the lens 41, between the lens 41 and the sample cell chamber 40. The spatial filter 42 may be of conventional design for blocking scattered light and thereby removing spatial noise. More particularly, the illustrative spatial filter 42 includes a mask 44 including a center opening 46 (illustratively having a diameter no greater than 3 millimeters) to allow only the laser beam 38 to pass therethrough, and blocking scattered laser light.

A first spectral filter 48 is illustratively positioned distal of the spatial filter 42. More particularly, the spectral filter 48 is illustratively positioned between the spatial filter 42 and the sample cell chamber 40. The spectral filter 48 may comprise a band-pass/interference filter that permits only radiation from the laser diode 36 to pass therethrough. For example, the spectral filter 48 allows only radiation (i.e., laser beam 38) of the laser diode 36 to pass therethrough (e.g., having a wavelength of about 275 nm+/−15 nm in the illustrative universal embodiment of biosensor 10).

The radiation emitting module 22 further includes a first or proximal power source 50 illustratively in electrical communication with the radiation emitting module 22. The first power source 50 may comprise a proximal battery 51 releasably supported within the end cap 34. The proximal battery 51 is illustratively a rechargeable button cell battery. In one illustrative embodiment, a military grade 3.0 Volt Saft BA5367U Lithium Sulfur Dioxide (1 inch×1 inch×0.075 inch) battery produced by Saft SA in France may be used. Another illustrative battery is the BA5367U battery together with a DC/DC High Voltage DBC-Series (0.83 inch×0.83 inch×0.32 inch) Module, available from Laser Components USA, for raising the voltage output.

A first or proximal power switch 52 is illustratively in electrical communication with the proximal battery 51 and is supported by the end cap 34 proximate the proximal end 16 of the outer casing 12. The proximal power switch 52 may be a toggle push button configured to be depressed by a user.

Figure 6A:
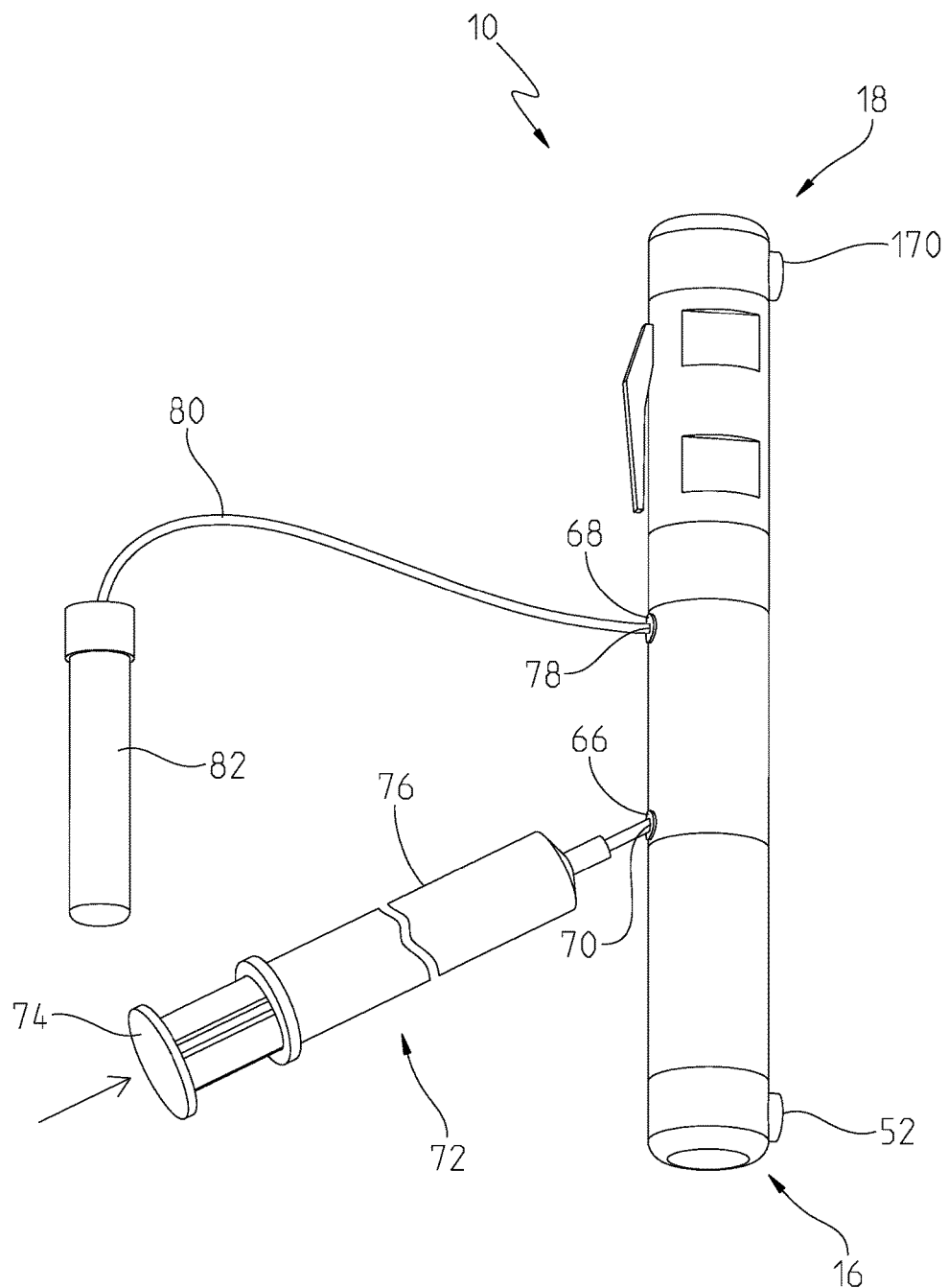
FIGS. 6A-6C are perspective views illustrating various steps of operation of the biosensor of FIG. 1.

The sample cell module 24 is illustratively positioned distal of the radiation emitting module 22 and includes a sample cell module housing 54 defining the sample cell chamber 40. A sample inlet 58 is positioned at a proximal end 60 of the housing 54 and is in selective fluid communication with the sample cell chamber 40. Similarly, a waste outlet 62 is positioned at a distal end 64 of the housing 54 and is in selective fluid communication with the sample cell chamber 40. Illustratively, both the sample inlet 58 and the waste outlet 62 may include a resilient septum 66 and 68, respectively. As further detailed herein, the septum 66 of the sample inlet 58 is configured to receive the tip 70 of a conventional syringe 72 including a plunger 74 slidably received within a barrel 76. Similarly, the septum 68 of the waste outlet 62 may receive the tip 78 of tubing 80 which is coupled to a collection device, such as a vial 82 (FIG. 6A).

The sample cell module housing 54 illustratively includes an outer cylindrical side wall 84 extending between the proximal end 60 and the distal end 64. A first or proximal end wall 90 is coupled to the proximal end 60 of the side wall 84, and a second or distal end wall 92 is coupled to the distal end 64 of the side wall 84. The side wall 84 and the end walls 90 and 92 are illustratively formed of a durable, light weight material, such as anodized aluminum or thermoplastic. The inner surface 100 of the sample cell chamber 40 is illustratively darkened, illustratively by application of a dark coating and/or texturing. More particularly, the inner surface 100 may be defined by the sidewall 84 and the end walls 90 and 92, and illustratively darkened for avoiding reflective and scattered light.

A light entry port 96 is illustratively formed within the proximal end wall 90, while a light exit port 98 is illustratively formed within the distal end wall 92. Illustratively, the light entry port 96 and the light exit port 98 are aligned along the longitudinal axis 14, and each has an illustrative diameter of about 5 millimeters centimeters (0.20 inches). The sample cell module housing 54 is illustratively sealed from external light, except for the light entry port 96 and the light exit port 98.

The sample cell module housing 54 illustratively defines a quartz sample cell chamber 40. An inner surface 100 of the sample cell module housing 54 may be textured for self-cleaning. In an illustrative embodiment, the inside surface 100 of the sample cell module housing 54 is nano-textured using, for example, ultra-short pulsed laser (USPL) beams or other known techniques to render the inner surface super-hydrophobic (i.e., water repelling) and/or super-lipophobic (i.e., repelling organic solvents/fats). The quartz sample cell chamber 40, as opposed to plastic vials or cells, reduces the chances of reaction and degradation, and promotes resulting prolonged usage and duration when used with various bio-agents. The walls of the quartz sample cell chamber 40 allows the laser light (illustratively 275 nm wavelength) and the fluorescence radiation (illustratively 345 nm wavelength) to pass through.

With further reference to FIGS. 3 and 4, a fluorescence detector 102 is illustratively supported adjacent a first side 104 of the sample cell module housing 54. More particularly, the fluorescence detector 102 may comprise a strip detector coupled to the side wall 84 of the sample cell module housing 54.

Illustratively, the fluorescence detector 102 is configured to detect electromagnetic radiation having a wavelength of interest, illustratively between 200 nm and 1000 nm. In one illustrative embodiment, the fluorescence detector 102 is configured to detect electromagnetic radiation having a wavelength of about 345 nm. In one illustrative embodiment, the fluorescence detector 102 is a high quantum-efficiency avalanche photodiode-array, such as 1.5 mm UV-VIS (200-1000 nm), Si APD, Stock No. 59-184, available from Edmund Optics Inc. of Barrington, N.J.

A fluorescence filter 106 is illustratively supported internally of the fluorescence detector 102. More particularly, the fluorescence filter 106 is illustratively positioned between the sample cell chamber 40 and the fluorescence detector 102. Illustratively, the fluorescence filter 106 comprises a spectral filter, such as a narrow band-pass filter configured to allow only fluorescence light of a wavelength of interest to pass therethrough. In an illustrative universal embodiment of the biosensor 10, the fluorescence filter 106 allows only radiation having a wavelength between about 295 nm and 420 nm, and more particularly about 345 nm, to pass therethrough.

A curved reflective surface 108 is illustratively supported adjacent a second side 110 of the sample cell module housing 54, opposite the fluorescence detector 102 adjacent the first side 104 of the sample cell module housing 54. Illustratively, the curved reflective surface 108 is defined by a polished surface or a mirror, illustratively a concave or spherical mirror 112 configured to curve-fit with the sample cell module housing 54. The mirror 112 is configured to collect and focus light or fluorescence emission 113 (FIG. 4) toward the fluorescence detector 102. The reflective surface 108 is illustratively configured to collect and focus light 113 with a wavelength of about 345 nm.

In the illustrative embodiment universal biosensor 10, the laser beam 38 is an electromagnetic radiation of approximately 275 nm wavelength, which is used to uniquely excite amino-acids tryptophan (Trp) and tyrosine (Tyr) in the sample solution in sample cell chamber 40. Fluorescence emission 113 (the 345 nm wavelength of light emitted from excited amino-acids tryptophan and tyrosine in this example) is collected with mirror 112 and reflected to the direction of the fluorescence detector 102. A blank solution within the sample cell chamber 40 generates no fluorescence detection, provides background from the fluorescence detector 102, and gives a background-subtracted zero fluorescence reading at a fluorescence display 150. Any fluorescence signals above zero represents detection at the fluorescence detector 102 of the 345 nm wavelength of light, characteristically representing the presence of amino-acids tryptophan and/or tyrosine in the sample solution within the sample cell chamber 40 and symbolizing detection of biomolecules.

A first releasable coupling 114 is positioned between the radiation emitting module 22 and the sample cell module 24. Illustratively, internal threads 116 on the distal end 33 of the radiation emitting module 22 engage external threads 118 on the proximal end 60 of the sample cell module 24. Other releasable couplings may be substituted for cooperating threads, including, for example bayonet couplings, resilient fingers, lock washers, etc.

The absorption detector module 26 illustratively includes an absorption detector module housing 120. The absorption detector module housing 120 illustratively includes a cylindrical side wall 122 extending between a proximal end 124 and a distal end 126. The side wall 122 is illustratively formed of a durable, light weight material, such as anodized aluminum or thermoplastic.

An absorption detector 128 is received within the absorption detector module housing 120, and is configured to detect emission intensity/energy produced by electromagnetic radiation passing through a solution in the sample cell chamber 40. In response, the detector 128 produces absorption spectral data. In an illustrative embodiment, the absorption detector 128 is an absorption spot detector. As further detailed herein, the absorption detector 128 in a universal embodiment of the biosensor 10 may comprise a deep ultraviolet (DUV) photodiode. Since the absorption detector 128 directly senses the laser beam, sensitivity is not an issue. In a selective embodiment of the biosensor 10 that employs a longer wavelength, a wide variety of known diodes are readily available.

Illustratively, the absorption detector 128 is configured to detect electromagnetic radiation having a wavelength of between about 200 nm and 980 nm, and more particularly a wavelength of about 275 nm. More particularly, the absorption detector 128 may comprise a silicon photodiode, such as 5.7 mm$^2$ DUV Photodiode with Ceramic Housing, Stock No. 84-982, available from Edmund Optics Inc. of Barrington, N.J.

A second spectral filter 130 is supported internally or proximal of the absorption detector 128. More particularly, the second spectral filter 130 is positioned between the sample cell chamber 40 and the absorption detector 128. The spectral filter 130 may comprise a band-pass/interference filter that permits only radiation from the laser diode 36 to pass therethrough. For example, the spectral filter 130 allows only radiation of the laser diode 36 (e.g., about 275 nm+/−15 nm in the illustrative universal embodiment of biosensor 10).

More particularly, the illustrative absorption detector 128 senses the intensity of the laser beam 38. In operation, the original intensity of the laser beam 38 (for example, 275 nm wavelength) passes through a blank solution in the sample cell chamber 40, is detected from the absorption detector 128, is registered and showed as zero absorption signal at an absorption display 152. An absorption signal higher than zero represents a partial absorption of the laser beam 38. The approximately 275 nm wavelength in this example indicates the presence of the amino acids tryptophan (Trp) and/or tyrosine (Tyr) in the sample solution in the sample cell chamber 40, and therefore, the presence of biomolecules.

The sample cell module 24 facilitates high sensitivity by providing a long absorption path length and a long emission (fluorescence) region. Absorption spectrophotometry is defined by Beer's Law according to the equation: $A = a \cdot b \cdot c$, where A is the absorbance signal (the remaining intensity of the source radiation detected), a is the unique spectral absorption of monochromatic source radiation (illustratively 275 nm laser light) for the example biomolecule at that wavelength, b is the absorption cell radiation path length, and c is the concentration of the sample solution.

As may be appreciated by Beer's Law, the absorbance signal (A) increases when the absorption cell radiation cell path length (b) increases. With reference to FIG. 4, the path length (b) of the sample cell in the illustrative biosensor is at least about 5 centimeters (1.96 inches). This path length provides improved signal strength of about five times over known biosensors having reduced path lengths (approximately 1 centimeter (0.39 inches)).

In fluorescence spectrophotometry, a molecule absorbs its unique excitation radiation and emits a red shifted characteristic radiation. The intensity of this emission is monitored by the fluorescence detector 102. Illustratively, a biomolecule absorbs laser light 38 of wavelength 275 nm and emit fluorescence light 113 of wavelength 345 nm.

Typically, with a fluorescence spectrophotometer, the emission from a sample cell having a volume less than 1 cm$^3$ (0.06 in$^3$) generated with diffused-lamp-excitation, is collected right-angle to the source-radiation and focused onto a spot-detector. The biosensor 10 of the present disclosure employs an intense, directional, laser-beam for optically-thin excitation of a relatively long (approximately 5 cm (1.96 inches)) sample path; and generates a long emission image that is collected at a right angle to the laser source by the concave reflective mirror (surface) 112 and focused onto the fluorescence strip detector 102. The detector and the emission image has an approximately overlapped dimension, resulting in high sensitivity.

As further detailed herein, the biosensor 10 may be used as a universal sensor for detecting all biomolecules, and/or a selective sensor for detecting only particular biomolecules. All biomolecules and biological cells (e.g., spores, human and bacterial cells, etc.) have proteins with their constituents being amino acids. Amino acids bond together to form proteins. The amino acids phenylalanine (Phe), tryptophan (Trp) and tyrosine (Tyr) can be monitored for "native" (i.e., label-free) absorption and fluorescence in response to electromagnetic radiation. With respect to the amount of amino acid found in protein: Phe>Tyr>Trp. As for the extinction coefficient for the amino acids: Trp>Tyr>Phe. The biosensor 10 detects the amino acids specifically and defines as a universal sensor for all biomolecules and biological cells.

When configured as an illustrative embodiment universal biosensor 10 for detecting both Trp and Tyr, the laser diode 36 illustratively emits an electromagnetic radiation or light having a wavelength of between about 265 nm and about 285 nm for the absorption measurement by the absorption detector 128. In one such illustrative embodiment, the laser diode 36 emits light having a wavelength of about 275 nm. An illustrative laser diode has an 8 to 10 mW output power, emitting a wavelength of 270 to 280 nm, such as model UVCLEAN275SMD available from QPhotonics of Ann Arbor, Mich.

The fluorescence measurement may illustratively be set between 295 nm and 420 nm, primarily for Trp. In one such illustrative embodiment, this is set at 345 nm through the fluorescence band-pass filter 106.

In the case for detecting Phe, the laser diode 36 illustratively emits electromagnetic radiation of about 255 nm for the absorption measurement and excitation, while about 280 nm is used for the fluorescence measurement.

As further detailed herein, the absorption detector 128 and the fluorescence detector 102 are illustratively deep ultraviolet (DUV) detectors. In alternative illustrative embodiments, the absorption detector 128 and the fluorescence detector 102 may each be a charge-coupled device (CCD) as used in camera and imaging devices.

When the illustrative biosensor 10 is configured as a selective sensor for only particular biomolecules, the laser diode 36 is selected with a suitable emission wavelength for detecting that biomolecule of interest. More particularly, in such a configuration, the biosensor 10 demonstrates increased selectivity and sensitivity for detection. As further detailed herein, the biomolecule of interest in the sample solution is dye-labeled prior to injection into the sample cell chamber 40. Certain organic-dyes or semi-conductor quantum dots preferentially bind to particular biomolecules/proteins. The dye-labeled or quantum dot-labeled protein has a characteristic absorption (excitation) and fluorescence (emission) wavelength profile.

In one illustrative embodiment of the biosensor 10 configured as a selective sensor, the laser diode 36 is configured to emit electromagnetic radiation having a wavelength of between about 400 nm and about 410 nm. The fluorescence measurement is 465 nm as defined by the fluorescence band-pass filter 106. The proper combination of laser diode 36 and filter 106 depends on the detection of the biomolecule(s) of interest. Modules or component sections are illustratively constructed for a particular application, for example, optimal wavelengths for excitation, and for absorption and fluorescence (detection) measurements.

A second releasable coupling 140 is positioned between the sample cell module 24 and the absorption detector module 26. Illustratively, internal threads 142 on the distal end 64 of the sample cell module 24 engage external threads 144 on the proximal end 124 of the absorption detector module 26. Other releasable couplings may be substituted for cooperating threads, including, for example bayonet couplings, resilient fingers, lock washers, etc.

A controller 145, including a processor 146 and a memory 147, is illustratively in electrical communication with the fluorescence detector 102 and the absorption detector 128. The memory 147 may include software and/or firmware containing instructions executed by processor 146 for controlling the radiation emitting module 22, the fluorescence detector 102, the absorption detector 128, the displays 150 and 152, and/or other components of the biosensor 10. The processor 146 may convert the fluorescence signal from the fluorescence detector 102 into a fluorescence reading on the fluorescence display 150. Similarly, the processor 146 may convert the absorption signal from the absorption detector 128 into an absorbance reading on the absorption display 152. The memory 147 may include a random-access memory configured to store information such as the date, locations, and the number of positive hits for particular biomolecules based upon the electromagnetic radiation wavelengths sensed by the detectors 102 and 128. An electrical coupler, for example a communication port or transmitter (not shown), may be operably coupled to the controller 145 for providing electrical communication with the processor 146 to supply data to external devices, for example.

The display module 28 is illustratively positioned distal of the absorption detector module 26 and includes a display module housing 148. Fluorescence display 150 is supported within the display module housing 148 and is configured to provide an indication of the fluorescence spectral data from the processor 146 as received from the fluorescence detector 102. Absorption display 152 is supported within the display module housing 148 and is configured to provide an indication of the absorption spectral data from the processor 146 as received from the absorption detector 128. The fluorescence display 150 illustratively comprises a digital readout (e.g., a liquid crystal display (LCD)) configured to display fluorescence spectral data from the processor 146 as received from the fluorescence detector 102. Similarly, the absorption display 152 illustratively comprises a digital readout (e.g., a liquid crystal display (LCD)) configured to display absorption data from the processor 146 as received from the absorption detector 128.

Different colors displayed by the display screens 150 and 152 (e.g., backlighting) may indicate the detection result from the target sample solution in the sample cell chamber 40. For example, green may represent no detectable signal (i.e., safe), yellow may represent a low detection signal (i.e., warning), and red may represent a significant detection signal (i.e., alarming). Illustratively, the intensity level of the display screens 150 and 152 are digital scales from 0 to 100, with threshold readings representing safe, warning, and alarming detection from the target sample.

Illustratively, the display module housing 148 includes a cylindrical side wall 154 extending between a proximal end 156 and a distal end 158. Illustratively, an end cap 160 is threadably coupled to the proximal end 156 of the side wall 154. Openings 162, 164 are formed within the side wall 154 and are aligned with the displays 150, 152. The display module 28 is in electrical communication with the processor 146. The displays 150, 152 and the processor 146 are illustratively coupled to a support, such as a printed circuit board (pcb) 166.

The display module 28 illustratively further includes a second or distal power source 168 in electrical communication with the processor 146, the displays 150, 152, the absorption detector 128, and the fluorescence detector 102. The second power source 168 illustratively comprises a distal battery 169 releasably supported within the end cap 160. The distal battery 169 is illustratively a rechargeable button cell battery. In one illustrative embodiment, a military grade 3.0 Volt Saft BA5367U Lithium Sulfur Dioxide (1 inch×1 inch×0.075 inch) battery produced by Saft SA in France may be used. Another illustrative battery is the BA5367U battery together with a DC/DC High Voltage DBC-Series (0.83 inch×0.83 inch×0.32 inch) Module available from Laser Components USA) for raising the voltage output.

A second or distal power switch 170 is illustratively in electrical communication with the distal battery 169 and is supported by the end cap 160 proximate the distal end 18 of the outer casing 12. The distal power switch 170 may be a toggle push button that is configured to be depressed by a user.

A third releasable coupling 172 is illustratively positioned between the display module 28 and the absorption detector module 26. Illustratively, internal threads 174 on the distal end 126 of the absorption detector module 26 engage external threads 176 on the proximal end 156 of the display module 28. Other releasable couplings may be substituted for cooperating threads, including, for example bayonet couplings, resilient fingers, lock washers, etc.

Wires may electrically couple the fluorescence detector, the processor 146 (and thereby the fluorescence display), and the distal battery. In certain illustrative embodiments, the releasable couplings 114, 140, 172 may include electrical couplers, such as spring contacts to provide electrical communication between the components in the radiation emitting module 22, the sample cell module 24, the absorption detector module 26, and the display module 28.

The modules 22, 24, 26, 28 are illustratively fitted or assembled into the functional form of the biosensor 10. More particularly, in the illustrative embodiment biosensor 10, the radiation emitting module housing 30, the sample cell chamber 40, the sample cell module housing 54, the absorption detection module housing 120 and the display module housing 148 cooperate to define the cylindrical outer casing 12. The releasable couplings 114, 140, 172 allow the modules 22, 24, 26, 28 to be separable, thereby facilitating the easy removal and replacement of components.

Figure 6B:
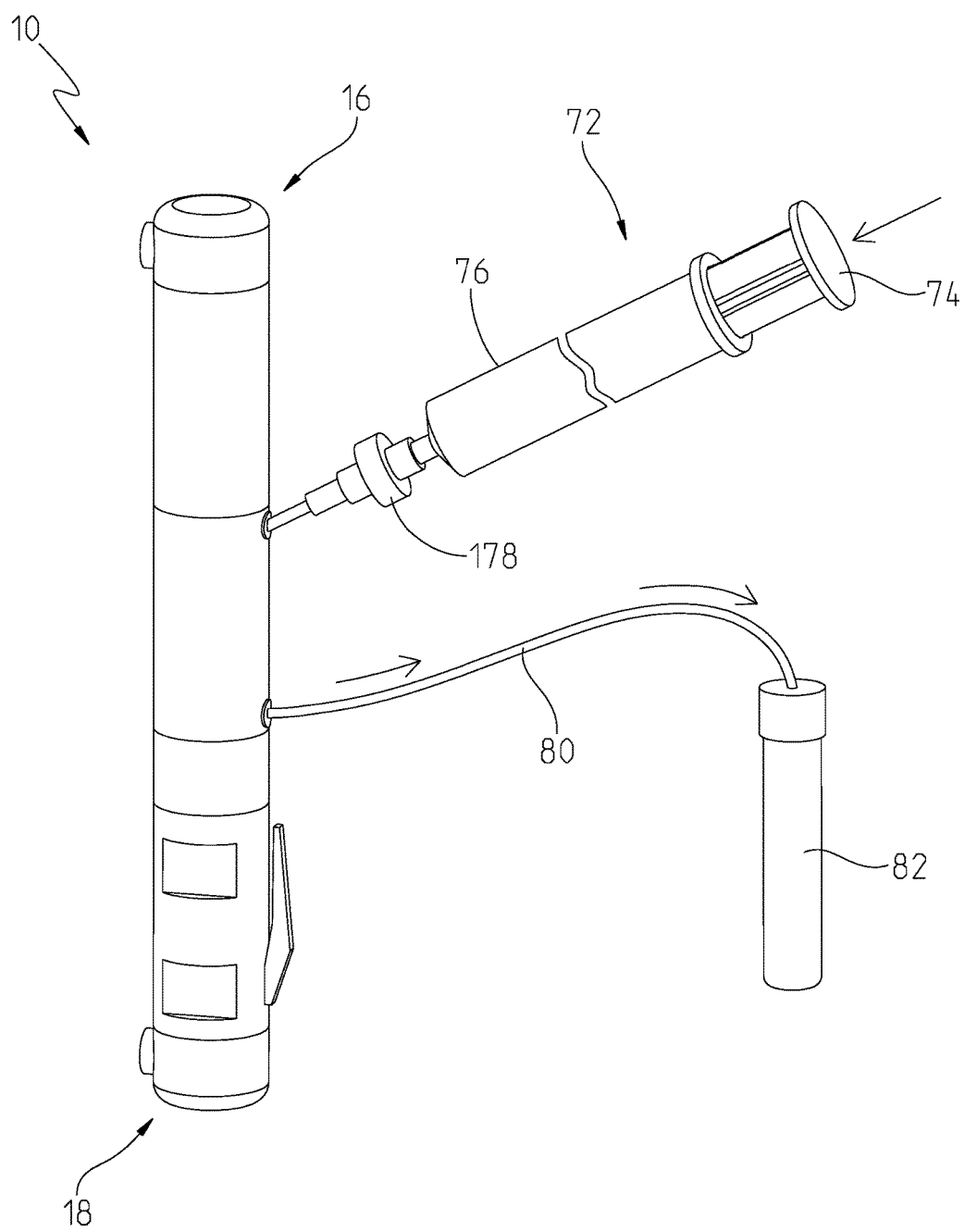
Figure 6C:
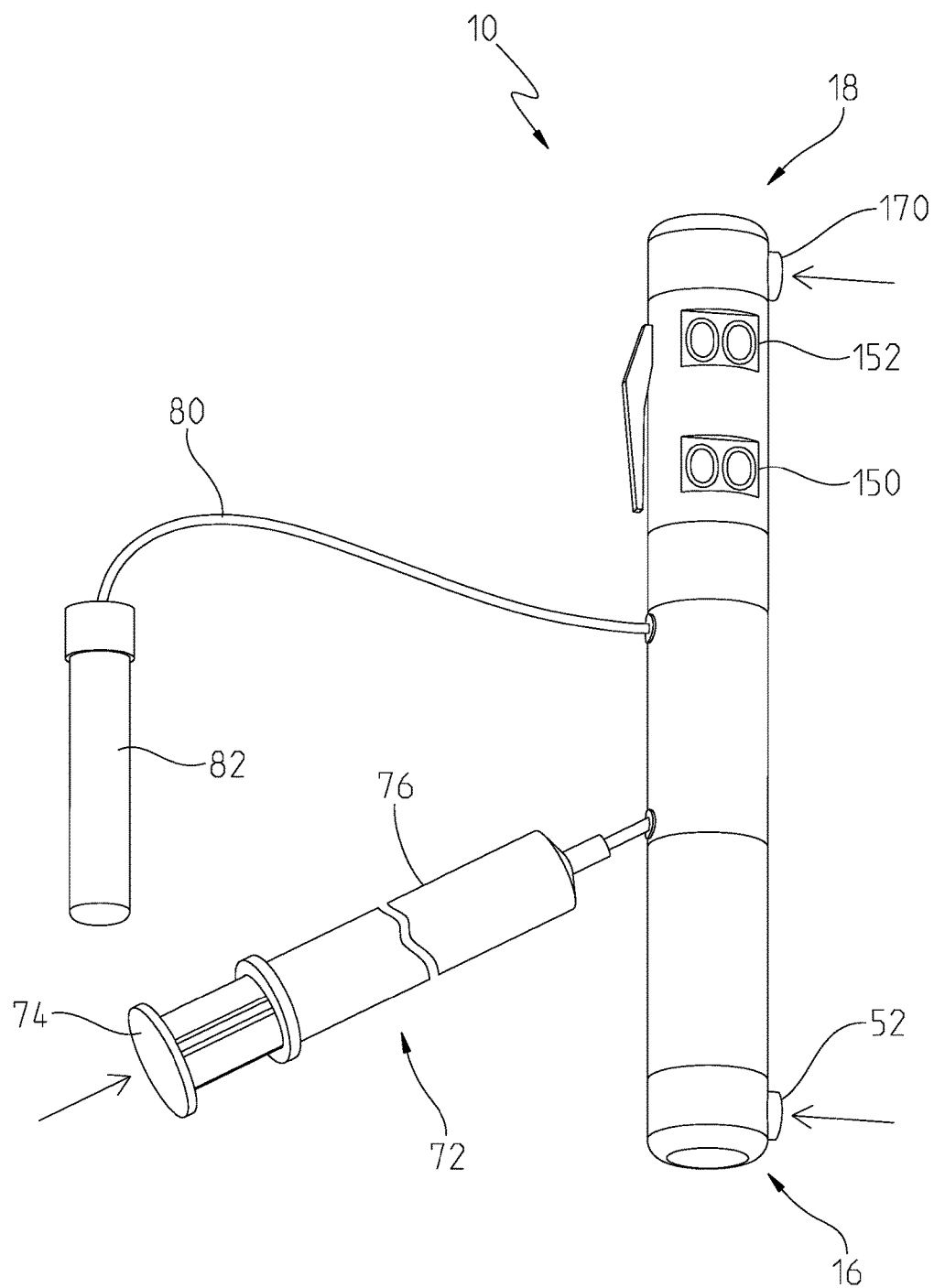

With reference to FIGS. 6A-6C, an illustrative method of operating the biosensor 10 of the present disclosure is disclosed. Initially, the biosensor 10 is oriented in an upright position with the longitudinal axis 14 extending in a vertical direction with the proximal end 16 positioned below the distal end 18. A waste adapter including tubing 80 and waste collection chamber or vial 82 is fluidly coupled to the sample cell chamber 40. More particularly, an end of the tubing 80 is fluidly coupled to the waste outlet 62.

Next, a cleansing solution (e.g., an alcohol-water mixture) of volume excess to (i.e., greater than) the volume of the sample cell chamber 40 is received within the barrel 76 of the syringe 72. The tip 70 of the syringe 72 is received within the septum 66 of the sample inlet 58 and the cleansing solution is injected into the sample cell chamber 40 by depressing the plunger 74 of the syringe 72. The excess cleansing solution flows out through the waste outlet 62 and into the collection vial 82.

The method continues by inverting the biosensor 10 to an inverted position such that the longitudinal axis 14 extends in a vertical direction with the distal end 18 positioned below the proximal end 16. Air is received within the barrel 76 by pulling the plunger 74 of the syringe 72 with the tip 70 engaged. A filter 178 is then attached between the syringe 72 and the tip 70. The tip 70 of the syringe 72 is received within the septum 66 of the sample inlet 58. Next, the plunger 74 is depressed thereby injecting filtered air into the sample cell chamber 40. The sample cell chamber 40 is evacuated by air forcing the residual cleansing solution out through the waste outlet 62 and into the waste vial 82, thereby helping to dry the inside surface of the sample cell chamber 40.

In the next step of the method, the biosensor 10 is returned to the upright position with the longitudinal axis 14 extending in a vertical direction with the proximal end 16 positioned below the distal end 18. A blank solution (e.g., water solution) is received within the barrel 76 of the syringe 72. The tip 70 of the syringe 72 is received within the septum 66 of the sample inlet 58. Next, the plunger 74 is depressed thereby injecting the blank into the sample cell chamber 40. The processor 146 will electronically generate zero absorbance at the absorption display 152 and zero signal at the fluorescence display 150. In one illustrative method, a sample solution is next received within the barrel 76 of the syringe 72. The tip 70 of the syringe 72 is received within the septum 66 of the sample inlet 58. Next, the plunger 74 is depressed thereby injecting the sample solution into the sample cell chamber 40.

In another illustrative method, a filtered sample solution is received within the barrel 76 by pulling the plunger 74 with a filter 178 attached between the syringe 72 and the tip 70 received in the sample solution. The filter 178 is then detached. The tip 70 of the syringe 72 is received within the septum 66 of the sample inlet 58. Next, the plunger 74 is depressed thereby injecting the filtered sample solution into the sample cell chamber 40.

The blank solution or the sample solution is illustratively injected into the sample cell chamber 40 within the sample inlet 58 to a volume level such that an excess volume of the sample solution comes out of waste outlet 62.

The method continues by the user depressing the power buttons 52, 170 to "on" positions, thereby activating the radiation emitting module 22, the display module 28, the fluorescence detector 102 and the absorption detector 128. The laser diode 36 emits electromagnetic radiation, illustratively light (e.g., laser beam 38), through the entry port 96 and the sample chamber 40. The light passes through the sample solution in the sample cell chamber 40, where the absorption portion of the light (i.e., intensity of the laser beam 38 absorbed by the sample solution) is directed to the exit port 98 and to the absorption detector 128, and the fluorescence portion of the light (i.e., intensity of excited or fluorescence emissions from the sample solution as a result of the laser beam 38) is reflected by the reflective surface 108 at a right angle to the electromagnetic radiation laser beam 38 (i.e., the longitudinal axis 14) to the fluorescence detector 102.

Absorption values from the absorption detector are transmitted to the processor 146 and then displayed on the absorption display 152. Fluorescence values from the fluorescence detector are transmitted to the processor 146 and then displayed on the fluorescence display 150. A baseline value can be set with the blank solution, where the display readings can be adjusted to zero values for background subtraction via the processor 146. Positive reading valves above zero indicate presence of biomolecules. The process may then continue by returning to the step of injecting the cleansing solution via the syringe 72.

As detailed above the outer dimensions of the biosensor 10 are relatively small. More particularly, the biosensor 10 is of a small size and is light weight, similar to those of a pen/laser pointer. The biosensor 10 also includes the capability to provide both absorption and fluorescence measurements simultaneously in of a field acquired sample solution. The biosensor 10 may find utility in a variety of applications, including in the military, food and health industries, and with first responders.

As further detailed herein, the biosensor 10 of the present disclosure facilitates portability by having a small size, being light weight, being durable, having low power requirements and being pocket wearable. The biosensor 10 includes modular components thereby allowing choices of integration into a variety of different purpose specific biosensors.

The biosensor 10 of the present disclosure provides for improved selectivity. More particularly, the biosensor 10 provides for selective detection based on combined molecular absorption spectrophotometry (MAS) and molecular fluorescence spectrophotometry (MFS). A higher signal reading is obtainable, due in part to the long path of laser beam-sample interactive, either from absorption detection or fluorescence detection, compared to "solo" operation (i.e., absorption detection or fluorescence detection alone). Some molecules favor the absorption process and other molecules favor the fluorescence process, due to either spectral or fundamental interactions, generating a higher combined signal.

The biosensor 10 of the present disclosure also provides for improved sensitivity. More particularly, the biosensor 10 provides for high sensitivity from the sample cell including a long absorption path length and a long emission (fluorescence) region. Additionally, the biosensor 10 operates with a laser beam, sample cell, and detectors enclosed in a light sealed assembly to prevent the detectors receiving interference from external light sources. Further, the sample cell of the biosensor may be recalibrated (i.e., zeroed) by using a blank solution or empty sample cell chamber, resulting in a higher signal-to-noise ratio, thereby increasing the sensitivity of the biosensor 10.

Further, the biosensor 10 is easy to operate with minimal or no sample preparation required. Simply inject an excess volume of a sample, and activate the power buttons to operate the biosensor 10.

The biosensor 10 demonstrates reliability by providing simple to read displays, providing repeatable performance with no operator interpretation required in reading results.

Additionally, the occurrence of false or incorrect results is easily identifiable. In addition to potential molecular spectral interference, the absorption measurement may receive interference by beam-blockage from opaque particles and the fluorescence (emission) measurement may receive interference by beam-scattering from reflective particles. Receiving an absorption reading but not a fluorescence reading, or vice versa, may be an indication of a possible false/incorrect result. Therefore, having both an absorption reading and a fluorescence reading works as a double-assurance, thereby increasing the confidence on each result of the biosensor.

Native absorption and fluorescence provides a major advantage for biomolecule detection because all biomolecules contain amino acids (e.g., phenylalanine, tryptophan, and tyrosine) and, therefore, by laser or appropriate light exposure directly on the sample solution followed by simultaneous positive absorption detection and positive fluorescence detection indicate the presence of biomolecules (e.g., phenylalanine, tryptophan, and tyrosine). That is, tryptophan and tyrosine characteristically absorb the laser or light wavelength of 275 nm and, when excited, emit their fluorescence radiation at 345 nm.

Additionally, operation of the biosensor 10 of the present disclosure provides for improved assay time. Simply activate the power buttons and read the displays which provide instance results in the field. The components of the biosensor are relatively inexpensive, thereby providing for a cost low enough for wide distribution.

The modular design of the biosensor 10 provides component choices. Assembling particular modules making the biosensor 10 functions as a universal biosensor for all biomolecules (based on native molecular absorption spectrophotometry and native fluorescence spectrophotometry) or as a selective biosensor (based on specific-tagging of selective biomolecules followed by characteristic absorption and fluorescence from the tagged biomolecules).

As detailed herein, theoretically, all biomolecules are composed an amount of amino acids tryptophan and tyrosine. Spectrally, tryptophan and tyrosine uniquely absorb light energy of approximately 275 nm wavelength, get excited and subsequently emit their characteristic fluorescence of approximately 345 nm wavelength. Operatively as a biosensor, the laser diode 36 emits an electromagnetic radiation (e.g., laser beam 38) of approximately 275 nm wavelength that is directed to pass through a sample in the sample cell chamber 40. The absorption detector 128 senses the intensity of the laser beam 38 (275 nm wavelength) absorbed, and the fluorescence detector 102 detects the collected light intensity, specifically of approximately 345 nm wavelength, emitted from the sample solution. A positive detection (signal above background from a blank solution) from the detectors 102 and 128 indicates the sample solution contains biomolecules.

Although the invention has been described in detail with reference to certain preferred embodiments, variations and modifications exist within the spirit and scope of the invention as described and defined in the following claims.

The invention claimed is:
1. A hand-held biosensor comprising:
a radiation emitting module including a radiation emitting module housing, a light source received within the radiation emitting module housing and configured to generate electromagnetic radiation;
a sample cell module including a sample cell module housing defining a chamber configured to receive a solution, a sample inlet in fluid communication with the chamber, and a waste outlet in fluid communication with the chamber;
a first releasable coupling between the radiation emitting module and the sample cell module;
an absorption detector configured to detect emission intensity produced by the electromagnetic radiation passing through the solution in the sample cell chamber and produce absorption spectral data in response thereto, the absorption detector including an absorption detector spectral filter;
a fluorescence detector configured to detect molecular emissions produced by the electromagnetic radiation passing through the solution in the sample cell chamber and produce fluorescence spectral data in response thereto, the fluorescence detector including a fluorescence detector spectral filter;
a processor in electrical communication with the absorption detector and the fluorescence detector, the processor configured to receive absorption spectral data from the absorption detector and fluorescence spectral data from the fluorescence detector;
a display module in electrical communication with the processor, the display module including a display module housing, an absorption display supported within the display module housing and configured to provide an indication of the absorption spectral data from the absorption detector, and a fluorescence display supported within the display module housing and configured to provide an indication of the fluorescence spectral data from the fluorescence detector;
a power source in electrical communication with the processor; and
a second releasable coupling between the display module and the sample cell module.

2. The hand-held biosensor of claim 1, wherein the light source comprises a laser diode.

3. The hand-held biosensor of claim 1, further comprising an absorption detection module including an absorption detection module housing receiving the absorption detector, and a third releasable coupling between the absorption detection module and the sample cell module, wherein the second releasable coupling is between the display module and the absorption detection module.

4. The hand-held biosensor of claim 3, wherein the radiation emitting module housing, the display module housing, and the absorption detection module housing cooperate to define a cylindrical outer casing.

5. The hand-held biosensor of claim 4, wherein the cylindrical outer casing extends between a proximal end and a distal end, the outer casing having an axial length of about 20 centimeters and a diameter of about 4 centimeters.

6. The hand-held biosensor of claim 5, further comprising an external clip coupled proximate the distal end of the outer casing.

7. The hand-held biosensor of claim 5, wherein the power source includes a proximal battery and a power switch positioned proximate the proximal end of the outer casing.

8. The hand-held biosensor of claim 7, wherein the power source includes a distal battery and a power switch positioned proximate the distal end of the outer casing.

9. The hand-held biosensor of claim 3, wherein the first releasable coupling includes a threaded connection between the radiation emitting module housing and the sample cell module housing, the second releasable coupling includes a threaded connection between the display module housing and the absorption detection module housing, and the third releasable coupling includes a threaded connection between the absorption detection module housing and the sample cell module housing.

10. The hand-held biosensor of claim 1, wherein the sample cell module includes a light entry port, a light exit port axially spaced by the chamber from the light entry port, a longitudinal axis defined by the light entry port and the light exit port, and a reflective surface configured to reflect light transverse to the longitudinal axis.

11. The hand-held biosensor of claim 10, wherein the sample cell module includes an axial length between the light entry port and the light exit port, the axial length being at least 5 centimeters.

12. The hand-held biosensor of claim 10, wherein the sample cell is a quartz sample cell.

13. The hand-held biosensor of claim 1, wherein the sample inlet comprises a resilient septum configured to receive a sample syringe.

14. A hand-held biosensor comprising:
an outer casing extending between a proximal end and a distal end;
a radiation emitting module supported proximate the proximal end of the outer casing;
a display module supported proximate the distal end of the outer casing;
a sample cell module supported intermediate the radiation emitting module and the display module;
the sample cell module including a sample cell module housing defining a chamber and including a light entry port, a light exit port axially spaced by the chamber from the light entry port, a longitudinal axis defined by the light entry port and the light exit port, and a reflective surface configured to reflect light transverse to the longitudinal axis;
an absorption detector;
a fluorescence detector;
a processor in electrical communication with the absorption detector and the fluorescence detector, the processor configured to receive absorption spectral data from the absorption detector and fluorescence spectral data from the fluorescence detector; and
wherein the sample cell module includes an axial length between the light entry port and the light exit port, the axial length being at least 5 centimeters.

15. The hand-held biosensor of claim 14, wherein:
the radiation emitting module includes a radiation emitting module housing, a light source received within the radiation emitting module housing and configured to generate an excitation energy; and
the display module includes a display module housing, an absorption display supported by the display module housing and configured to provide an indication of the absorption spectral data, and a fluorescence display supported by the display module housing and configured to provide an indication of the fluorescence spectral data.

16. The hand-held biosensor of claim 15, further comprising:
a first releasable coupling between the radiation emitting module and the sample cell module; and
a second releasable coupling between the display module and the sample cell module.

17. The hand-held biosensor of claim 16, further comprising an absorption detection module including an absorption detection module housing receiving the absorption detector, and a third releasable coupling between the absorption detection module and the sample cell module, wherein the second releasable coupling is between the display module and the absorption detection module.

18. The hand-held biosensor of claim 17, wherein the first releasable coupling includes a threaded connection between the radiation emitting module housing and the sample cell module housing, the second releasable coupling includes a threaded connection between the display module housing and the absorption detection module housing, and the third releasable coupling includes a threaded connection between the absorption detection module housing and the sample cell module housing.

19. The hand-held biosensor of claim 18, wherein the radiation emitting module housing, the sample cell module housing, the display module housing, and the absorption detection module housing cooperate to define the outer casing.

20. The hand-held biosensor of claim 19, wherein the outer casing is cylindrical and extends between a proximal end and a distal end, the outer casing having an axial length of about 20 centimeters and a diameter of about 4 centimeters.

21. The hand-held biosensor of claim 14, wherein the sample cell module includes an axial length between the light entry port and the light exit port, the axial length being at least 5 centimeters.

22. The hand-held biosensor of claim 21, wherein the sample cell is a quartz sample cell.

23. A method of constructing a hand-held biosensor, the method comprising the steps of:
providing a sample cell module including a sample cell module housing having a side wall defining a chamber and extending longitudinally between a proximal end and a distal end, a sample inlet in fluid communication with the chamber, and a waste outlet in fluid communication with the chamber;
providing a solution within the chamber of the sample cell module;
providing a radiation emitting module including a radiation emitting module housing extending longitudinally between a proximal end and a distal end, a light source received within the radiation emitting module housing and configured to generate electromagnetic radiation;
releasably coupling the distal end of the radiation emitting module housing to the proximal end of the sample cell module housing;
providing an absorption detector at the distal end of the sample cell, the absorption detector configured to detect emission intensity produced by the electromagnetic radiation passing through the solution in the sample cell chamber, the absorption detector including an absorption detector spectral filter;
providing a fluorescence detector configured to detect molecular emissions produced by the electromagnetic radiation passing through the solution in the sample cell chamber, the fluorescence detector including a fluorescence detector spectral filter;
providing a processor in electrical communication with the absorption detector and the fluorescence detector, the processor configured to receive absorption spectral data from the absorption detector and fluorescence spectral data from the fluorescence detector;
providing a display module in electrical communication with the processor, the display module including a display module housing extending between a proximal end and a distal end, an absorption display supported within the display module housing and configured to provide an indication of the absorption spectral data, and a fluorescence display supported within the display module housing and configured to provide an indication of the fluorescence spectral data;
releasably coupling the distal end of the sample cell module housing to the proximal end of the display module housing; and
providing a power source in electrical communication with the processor.

24. The method of claim 23, wherein the light source comprises a laser diode and a laser diode driver operably coupled to the laser diode, the laser diode configured to project light to a lens.

25. The method of claim 23, wherein the steps of:
releasably coupling the distal end of the radiation emitting module housing to the proximal end of the sample cell module housing includes threadably coupling the radiation emitting module housing with the sample cell module housing; and
releasably coupling the distal end of the sample cell module housing to the proximal end of the display module housing includes threadably coupling the sample cell module housing with the display module housing.

26. The method of claim 23, further comprising the steps of:
providing an absorption detection module including an absorption detection module housing extending longitudinally between a proximal end and a distal end and receiving the absorption detector;
releasably coupling the distal end of the sample cell module housing with the proximal end of the absorption detection module housing; and
releasably coupling the distal end of the absorption detection module housing module and the proximal end of the display module housing.

27. The method of claim 26, wherein:
the radiation emitting module housing, the sample cell module housing, the display module housing, and the absorption detection module housing cooperate to define a cylindrical outer casing; and the outer casing extends between a proximal end and a distal end, the outer casing having an axial length of about 20 centimeters and a diameter of about 4 centimeters.

28. The method of claim 23, wherein the sample cell module includes a light entry port, a light exit port axially spaced by the chamber from the light entry port, a longitudinal axis defined by the light entry port and the light exit port, and a reflective surface configured to reflect light transverse to the longitudinal axis.

29. The method of claim 28, wherein the sample cell module includes an axial length between the light entry port and the light exit port, the axial length being at least 5 centimeters.

30. A method of detecting a substance within a fluid sample using a hand-held biosensor, the method comprising the steps of:
providing a sample cell module including a sample cell module housing having a side wall defining a chamber and extending a longitudinal axis between a proximal end and a distal end, a sample inlet in fluid communication with the chamber, and a waste outlet in fluid communication with the chamber;
fluidly coupling a waste collection vial to the waste outlet;
injecting a sample solution through the sample inlet into the chamber of the sample cell module;
generating electromagnetic radiation with a light source;

directing the electromagnetic radiation through the sample solution in the chamber of the sample cell;

absorbing the electromagnetic radiation by the sample solution;

sensing the intensity of the electromagnetic radiation absorbed by the sample solution by an absorption detector;

generating an absorption signal of interest from the absorption detector;

producing fluorescence emissions from the sample solution;

sensing the fluorescence emissions by a fluorescence detector;

generating a fluorescence signal of interest from the fluorescence detector;

displaying an indication of the absorption signal on an absorption display; and displaying an indication of the fluorescence signal on a fluorescence display.

31. The method of claim 30, further comprising the step of injecting a cleansing solution through the sample inlet prior to the step of injecting the sample solution.

32. The method of claim 31, further comprising the steps of inverting the sample cell, and injecting filtered air through the sample inlet port, and forcing the cleansing solution out through the waste outlet.

33. The method of claim 30, further comprising the step of contacting a first power user input to activate the light source.

34. The method of claim 33, further comprising the step of contacting a second power user input to activate the absorption detector, the fluorescence detector, the absorption display and the fluorescence display.

35. The method of claim 31, wherein the step of directing the excitation energy includes:

directing light parallel to a longitudinal axis through the chamber of the sample cell to the absorption detector; and reflecting light transverse to the longitudinal axis through the chamber of the sample cell to the fluorescence detector.

36. The method of claim 31, wherein the sample inlet includes a septum, and the step of injecting a sample solution through the sample inlet includes inserting a syringe into the septum.

37. The method of claim 31, wherein the light source is received within a radiation emitting module housing of a radiation emitting module, and further comprising the step of releasably coupling the radiation emitting module housing to the sample cell module housing.

38. The method of claim 37, wherein the absorption display and the fluorescence display are received within a display module housing of a display module, and further comprising the step of releasably coupling the display module housing to the sample cell module housing.

39. The method of claim 31, wherein the sample cell module includes a light entry port, a light exit port axially spaced by the chamber from the light entry port, a longitudinal axis defined by the light entry port and the light exit port, and a reflective surface configured to reflect light transverse to the longitudinal axis.

40. The method of claim 39, wherein the sample cell module includes an axial length between the light entry port and the light exit port, the axial length being at least 5 centimeters.

41. The method of claim 30, wherein the light source generates electromagnetic radiation for the sample solution having a wavelength of approximately 275 nm, and fluorescence emissions from the sample solution having a wavelength of approximately 345 nm.

42. The method of claim 41, wherein the light source comprises a laser diode and a laser diode driver operably coupled to the laser diode, the laser diode configured to project light to a lens.

43. The method of claim 41, further comprising a bandpass spectral filter to generate the selected fluorescence emissions having a wavelength of approximately 345 nm.

44. The method of claim 41, wherein the electromagnetic radiation having a wavelength of approximately 275 nm is absorbed by amino acids including tryptophan and tyrosine.

45. The method of claim 44, wherein tryptophan and tyrosine are excited on absorption of radiation having a wavelength of 275 nm.

46. The method of claim 45, wherein tryptophan and tyrosine emit fluorescence emissions having a wavelength of 345 nm.

* * * * *